United States Patent
Bartee et al.

(10) Patent No.: US 8,556,989 B2
(45) Date of Patent: Oct. 15, 2013

(54) HYDROPHILIC HIGH DENSITY PTFE MEDICAL BARRIER

(76) Inventors: Chad M. Bartee, Lubbock, TX (US); Barry K. Bartee, Lubbock, TX (US)

( * ) Notice: Subject to any disclaimer, the term of this patent is extended or adjusted under 35 U.S.C. 154(b) by 1031 days.

(21) Appl. No.: 11/941,060

(22) Filed: Nov. 15, 2007

(65) Prior Publication Data

US 2008/0133010 A1    Jun. 5, 2008

Related U.S. Application Data

(63) Continuation of application No. 10/947,066, filed on Sep. 21, 2004, now Pat. No. 7,296,998.

(60) Provisional application No. 60/505,093, filed on Sep. 22, 2003.

(51) Int. Cl.
*A61F 2/02*    (2006.01)

(52) U.S. Cl.
USPC .................................................. 623/23.72

(58) Field of Classification Search
USPC ............... 623/23.72, 23.76, 23.74, 23.5, 908; 433/173, 215
See application file for complete search history.

(56) References Cited

U.S. PATENT DOCUMENTS

| | | | |
|---|---|---|---|
| 4,531,916 A * | 7/1985 | Scantlebury et al. | 433/173 |
| 4,725,234 A * | 2/1988 | Ethridge | 433/215 |
| 4,885,077 A * | 12/1989 | Karakelle et al. | 204/403.06 |
| 4,909,244 A * | 3/1990 | Quarfoot et al. | 602/48 |
| 4,954,388 A * | 9/1990 | Mallouk et al. | 428/198 |
| 5,016,622 A * | 5/1991 | Norvell | 602/7 |
| 5,028,332 A * | 7/1991 | Ohnishi | 210/500.34 |
| 5,032,445 A * | 7/1991 | Scantlebury et al. | 428/158 |
| 5,036,551 A * | 8/1991 | Dailey et al. | 2/167 |
| 5,069,686 A * | 12/1991 | Baker et al. | 95/47 |
| 5,082,472 A * | 1/1992 | Mallouk et al. | 95/49 |
| 5,093,179 A * | 3/1992 | Scantlebury et al. | 428/158 |
| 5,118,524 A | 6/1992 | Thompson et al. | |
| 5,171,148 A * | 12/1992 | Wasserman et al. | 433/215 |
| 5,197,882 A * | 3/1993 | Jernberg | 433/215 |
| 5,206,028 A * | 4/1993 | Li | 424/484 |
| 5,264,214 A | 11/1993 | Rhee et al. | |
| 5,356,429 A * | 10/1994 | Seare | 623/8 |
| 5,378,152 A * | 1/1995 | Elia | 433/173 |
| 5,658,354 A * | 8/1997 | Norvell | 623/36 |
| 5,674,241 A * | 10/1997 | Bley et al. | 623/1.2 |
| 5,700,479 A * | 12/1997 | Lundgren | 424/435 |
| 5,728,169 A * | 3/1998 | Norvell | 623/36 |
| 5,798,117 A | 8/1998 | New et al. | |
| 5,837,278 A * | 11/1998 | Geistlich et al. | 424/444 |
| 5,957,690 A * | 9/1999 | Bartee et al. | 433/215 |
| 5,968,070 A * | 10/1999 | Bley et al. | 606/198 |
| 5,977,428 A * | 11/1999 | Bozigian et al. | 602/48 |
| 5,993,972 A * | 11/1999 | Reich et al. | 428/423.1 |
| 6,019,764 A * | 2/2000 | Bartee | 606/86 R |

(Continued)

*Primary Examiner* — Melanie Tyson
*Assistant Examiner* — Son Dang
(74) *Attorney, Agent, or Firm* — Pillsbury Winthrop Shaw Pittman LLP

(57) ABSTRACT

A medical barrier includes a sheet of unsintered substantially unexpanded hydrophilic polytetraflouroethylene (PTFE) polymer material. A PTFE polymer material is described that has a density in a range of about 1.2 gm/cc to about 2.3 gm/cc, and preferably in the range of about 1.45 gm/cc to about 1.55 gm/cc, and having at least one textured surface. In accordance with one embodiment, the sheet has one textured surface and one substantially smooth surface, and has substantially uniform strength in all directions.

21 Claims, 2 Drawing Sheets

(56) References Cited

U.S. PATENT DOCUMENTS

| | | | |
|---|---|---|---|
| 6,022,553 A * | 2/2000 | Anders et al. | 424/411 |
| 6,060,640 A * | 5/2000 | Pauley et al. | 623/23.72 |
| 6,143,946 A * | 11/2000 | Docter | 602/41 |
| 6,238,214 B1 * | 5/2001 | Robinson | 433/215 |
| 6,244,868 B1 * | 6/2001 | Schappert | 433/173 |
| 6,264,702 B1 * | 7/2001 | Ory et al. | 623/23.75 |
| 6,270,530 B1 * | 8/2001 | Eldridge et al. | 623/23.74 |
| 6,277,150 B1 * | 8/2001 | Crawley et al. | 623/17.18 |
| 6,325,627 B1 * | 12/2001 | Ashman | 433/173 |
| 6,328,765 B1 * | 12/2001 | Hardwick et al. | 623/23.72 |
| 6,409,764 B1 | 6/2002 | White et al. | |
| 6,420,623 B2 * | 7/2002 | Augustine et al. | 602/41 |
| 7,296,998 B2 * | 11/2007 | Bartee et al. | 433/215 |
| 7,789,888 B2 * | 9/2010 | Bartee et al. | 606/151 |
| 2002/0197924 A1 * | 12/2002 | Halley et al. | 442/148 |
| 2003/0040809 A1 * | 2/2003 | Goldmann et al. | 623/23.76 |
| 2003/0104734 A1 * | 6/2003 | Polegato Moretti | 442/1 |
| 2004/0215219 A1 * | 10/2004 | Eldridge et al. | 606/151 |
| 2005/0102036 A1 * | 5/2005 | Bartee et al. | 623/23.76 |
| 2007/0260268 A1 * | 11/2007 | Bartee et al. | 606/151 |
| 2010/0234880 A1 * | 9/2010 | Abbott et al. | 606/213 |

* cited by examiner

HYDROPHILIC HIGH DENSITY PTFE MEDICAL BARRIER

CROSS-REFERENCE TO RELATED APPLICATION

The present application is a continuation of allowed U.S. patent application Ser. No. 10/947,066, filed Sep. 21, 2004, now U.S. Pat. No. 7,296,998 entitled "HYDROPHILIC HIGH DENSITY PTFE MEDICAL BARRIER," which claimed the benefit of now-expired U.S. provisional application Ser. No. 60/505,093, filed Sep. 22, 2003, entitled "HYDROPHILIC HIGH DENSITY PTFE MEDICAL BARRIER," the disclosures of which applications are hereby incorporated herein by reference in their entirety.

FIELD OF THE INVENTION

Aspects of the present invention relate generally to implantable medical products and more particularly to a hydrophilic high density polytetrafluoroethylene (PTFE) medical barrier for use in guided tissue regeneration in the repair of bone defects, and particularly in the repair of alveolar and maxillofacial bone defects.

BACKGROUND

The basic concepts which led to the clinical procedure of guided tissue regeneration were reported by Melcher in 1976 in the Journal of Periodontics. This work identified four distinct connective tissue cell phenotypes in the periodontium; the gingival corium, periodontal ligament, cementum and bone. Melcher proposed that the healing response that occurs after wounding is dependent on the phenotype of cells that repopulate the area. With the knowledge that epithelial cells from the gingival soft tissues would proliferate at a faster rate than bone or periodontal ligament cells, the early efforts at guided tissue regeneration focused on epithelial exclusion by various mechanical means, including the placement of a thin sheet of biocompatible material between the bone defect and overlying soft tissue. Histological evaluation of animal tissues confirmed the hypothesis that if the more aggressive and faster growing gingival epithelial cells were prevented from entering a periodontal bone defect during the healing phase, then new cementum, bone, and periodontal ligament would be formed from undifferentiated mesenchymal cells originating from the adjacent bone, cementum and bone marrow would selectively repopulate the defect.

At present, there is significant interest in the repair and regeneration of bony defects that may result from surgery such as the removal of cysts, the removal of tooth roots, bone loss from infection or inflammatory process around teeth or dental implants, bone atrophy, trauma, tumors or congenital defects. Bone loss may result in pain, loss of function, mobility and subsequent loss of teeth, mobility and subsequent loss of dental implants, and recurrent infections. Additionally, deficient bone volume precludes adequate prosthetic reconstruction. Wound healing studies indicate that the most complete healing of oral and maxillofacial bone defects occurs when gingival epithelial and connective tissue cells are prevented from entering the bony defect.

There are several commercially available products that have been used successfully as guided tissue regeneration membranes, including those made from expanded polytetrafluoroethylene (PTFE), high density PTFE, bovine type I collagen, polylactide/polyglycolide co-polymers, calcium sulfate and even human skin. A review of the scientific literature indicates that no single ideal membrane material exists, but that each type of product has its own advantages and disadvantages.

An example of a current commercially available product employs a low-density expanded version of polytetrafluoroethylene (ePTFE) which presents a open-structure matrix to the gingival epithelial and connective tissue cells. This expanded version of PTFE is characterized by a low density of about 1.0 gm/cc or less and a porous, hydrophobic surface. In spite of the hydrophobic surface, soft tissue cells readily incorporate into the expanded matrix due to the open, porous structure of the material. While this connective tissue ingrowth is said to effectively prevent the migration of epilthelial cells, it presents a difficult problem to the patient and surgeon in the later stages of the regenerative procedure. After several weeks to several months, the non-absorbable low-density hydrophobic ePTFE barrier membrane must be removed. The incorporated cells and fibrous connective tissue make removal painful and traumatic to the patient and very time-consuming for the surgeon. The low-density open-matrix design of ePTFE devices also provides a location for the ingress of food particles, bacteria, and other foreign bodies which, in turn, create post-operative problems with the device such as inflammation, infection, wide exposure of the barrier material with wound dehiscence, and gingival recession. Any of these complications may require early removal of the barrier material, therefore compromising the treatment outcome. Low-density open-matrix or open-structure materials are generally soft and flimsy such that they will not mechanically support tissue above the defect during normal functional activities within the mouth causing a breakdown of the barrier's effectiveness. The articles described by Scantlebury, et. al. in U.S. Pat. Nos. 5,032,445 and 4,531,916 are such ePTFE devices.

Other products incorporate bio-absorbable polymer technology into their design. Such products are made from dense collagen matrices of human or bovine origin, which are broken down via hydrolysis and absorbed into the body fluids following several weeks to several months of implantation. While such devices eliminate the need for a second surgical procedure to remove them, some patients may exhibit a vigorous antigenic response to the devices which delays and often prevents the desired healing process within the defect, and may cause dehiscence of sutured wounds. Even in the absence of a specific antigenic response to implanted collagen, breakdown and resorption of these devices often results in generalized inflammatory cascade including neutrophil and macrophage activation. This foreign-body response also produces undesirable effects with regard to healing kinetics and pain. Bio-resorption time also varies significantly from patient to patient, presenting both patient and surgeon with an uncertainty regarding overall healing rate and pain management. Examples of collagen membranes in the literature are BioMend® and BioGide®. The articles described by Li in U.S. Pat. No. 5,206,028 and Geistlich in U.S. Pat. No. 5,837,278 are examples of such devices.

Synthetic polymers of lactide, glycolide and their various copolymers are also used as guided tissue regeneration barriers. These materials are biodegradable and offer the benefits of avoiding a surgical procedure for their removal. However, use of these materials results in inflammatory responses similar to those seen with naturally derived polymers such as collagen. In addition, the resorption profile may be unpredictable from patient to patient. These materials are also highly porous which renders them susceptible to bacterial colonization and contamination with foreign materials in the oral cavity in the event of exposure. A synthetic membrane barrier exhibiting similar characteristics is Vicryl® (polyglactin) periodontal mesh, Resolute® periodontal membrane described by Hayes et al, in U.S. Pat. No. 6,031,138 and Cytoplast® Resorb regenerative membrane.

Other products used as surgical membranes for the treatment of jaw and alveolar bone defects are human freeze-dried laminar bone and human freeze-dried dura mater obtained from human cadavers. These materials are bio-absorbable and osteoconductive, but carry a small but unknown risk of human disease transmission from donor to host. The risk of disease transmission precludes the use of this material by many surgeons and patients.

In an effort to provide a material with the biocompatibility and chemical inertness of PTFE but without the disadvantages of the porous open surface structure of expanded PTFE, a high density PTFE membrane material has been used and has achieved widespread clinical acceptance.

In U.S. Pat. No. 5,957,690 and U.S. Pat. No. 6,019,764 the use of a flexible high-density polytetrafluoroethylene (PTFE) sheet material was disclosed as a material suitable for guided tissue regeneration procedures. High density PTFE is substantially nonporous or microporous so as not to incorporate cells or attach to fibrous adhesions. By presenting a smooth surface to the biological materials, a high density PTFE barrier is easily inserted and removed following extended implantation periods. A similar high density PTFE barrier material is disclosed in U.S. Pat. No. 5,480,711. Examples of such products used for guided tissue regeneration include smooth and textured surface, hydrophobic high density PTFE such as Cytoplast®Regentex and TefGenFD®.

While high density PTFE medical barriers provide advantages over macroporous barriers, the smooth surface of the high density PTFE barriers sometimes leads to dehiscence of the soft tissue overlying the barrier. The dehiscence problem is caused in part by the fact that the smooth surface of high density PTFE will not incorporate cells and will not attach to fibrous adhesions as compared to expanded PTFE.

An additional clinical problem exhibited by high density PTFE is related to its hydrophobicity, or tendency to repel water. The chemical composition and resulting surface chemistry of a material determine its interaction with water. Hydrophobic materials have little or no tendency to adsorb water and water tends to "bead" on their surfaces in discrete droplets. Hydrophobic materials possess low surface tension values and lack active groups in their surface chemistry for formation of "hydrogen-bonds" with water. In the natural state, PTFE exhibits hydrophobic characteristics, which requires surface modification to render it hydrophilic. All previously disclosed products, whether constructed from expanded PTFE or high density PTFE have such hydrophobic characteristics.

It is well known in the art that biomaterial surfaces exhibiting hydrophobic characteristics are less attractive in terms of cell attachment. This is an advantage in some respects, as it prevents the ready attachment and migration of certain bacteria into the interstices of the material. However, in terms of interaction with host tissue, this characteristic may be less desirable and may contribute to dehiscence, or loss of soft tissue covering over the membrane during the course of healing. Dehiscence is a common clinical complication of guided tissue regeneration therapy, with an incidence of up to 60% according to the published literature. The clinical sequelae may indeed be serious, resulting in infection and failure of the procedure. The dehiscence phenomenon has been observed with both high density and expanded PTFE membrane devices, both of which to date have only been available with hydrophobic surfaces.

Although there are no reports of hydrophilic PTFE used in the construction of guided tissue regeneration membranes or similar implantable devices, hydrophilic, surface modified PTFE has a history of use as a filter in applications such as basic chemical and laboratory filtration, water purification, filtration of intravenous lines, blood oxygenators and extracorporeal hemofiltration devices.

U.S. Pat. No. 5,282,965 relates to a hydrophilic porous fluorocarbon membrane filter for liquids, which is used in microfiltration or ultrafiltration of liquids such as chemicals and water, and to a filtering device using said membrane filter. The filter is treated with low temperature plasma (glow discharge) to create a hydrophilic surface. Specifically this invention relates to a membrane filter for liquids, which is suitably used to filtrate chemicals for washing silicon wafers in semiconductor industries, and to a filtering device.

A hydrophilic semi-permeable PTFE membrane is disclosed in U.S. Pat. No. 5,041,225. This invention describes hydrophilic, semi-permeable membranes of PTFE and their manufacture, and further describes membranes suitable for use in body fluid diagnostic test strips and cell support members. In this instance, the intent of the hydrophilic membrane is to cover the target area of a diagnostic test strip with a semi-permeable membrane of a controlled pore size so that a fluid sample applied to such a membrane be applied in a controlled manner through the membrane to the underlying reagents. It should be noted that this invention discloses an in-vitro device and does not mention or anticipate use as a surgical implant.

Hydrophilic polymer membranes have been developed for use in the pharmaceutical industry as disclosed in U.S. Pat. No. 5,573,668 which describes a hydrophilic microporous membrane for drug delivery and a method for its preparation. Hydrophilicity is achieved by the application of a thin hydrophilic polymer shell, where the shell does not substantially alter the complex geometry of the membrane. Typically, drug delivery devices of non-resorbable polymers such as described in this patent are placed on the skin with adhesive, and are not surgically implanted.

Hydrophilic polymer membranes, which are biocompatible, antithrombogenic, and incorporate functional groups for immobilization of bioactive molecules are disclosed in U.S. Pat. No. 5,840,190. Specifically, this patent deals with membrane separators used in machines involved in the extracorporeal circulation of blood such as heart-lung machine oxygenators, hemofiltration units of dialysis machines, invasive blood gas sensors and artificial organs such as artificial pancreas and skin.

There are two methods described in this patent for fabrication of these surface modified membranes. "Method A" describes preparation of a casting solution containing the membrane forming polymer and then precipitating the casting solution in a bath containing the surface modifying polymer. "Method B" describes preparation of the casting solution containing the membrane forming polymer as well as the surface modifying polymer, and then precipitating the membrane from the casting solution in a coagulation bath. While this method may work with many polymers, including cellulose, cellulose acetate, polysulfone, polyamide, polyacrylonitrile, and polymethylmethacrylate, neither method is feasible with PTFE. Further, there is no mention of PTFE within the text or claims of this patent.

A method for coating a hydrophobic polymer so as to render said membrane hydrophilic is disclosed in U.S. Pat. No. 4,525,374. This method is said to be particularly for treating polypropylene or polytetrafluoroethylene in which the filter membrane is contemplated to have a pore size not larger than two (2) microns. The treating solution has Triethanolamine Dodecylbenzene Sulfonate (LAS) as the active ingredient. Treatment of expanded PTFE filters such as Poreflon® and GoreTex® are described in the context of filters for various chemical fluids such as intravenous fluids. There is no disclosure of use of said devices as a medical implant or guided tissue regeneration membrane.

A number of challenges are encountered in the design of the ideal GTR barrier. For example, the membrane must be dense enough to resist passage of unwanted cells such as epithelial cells and bacteria, yet be able to allow the passage of biological fluids, oxygen and nutrients required to sustain the viability of the regenerated tissue as well as the overlying tissue. The porosity of currently available products varies widely, from fully dense to over 30 microns in average pore size. According to the literature, those with larger pore size typically have a higher infection rate in clinical use. In contrast, the fully dense materials, while exhibiting superior characteristics in terms of infection resistance, are criticized due to the concern that they are unable to conduct the passage of nutrients in an efficient manner. Thus, there is a need for an improved membrane material of sufficient density to prevent the ingress of unwanted cells and bacteria, and yet be able to readily allow passage of biological fluids, molecules and oxygen.

A second major design issue involves the surface macrogeometry. The barrier membrane must be smooth enough to achieve a high degree of biocompatibility, yet must integrate well with the surrounding tissue to achieve clinical stability. Current products, with the exception of smooth surface dense PTFE membranes, rely on a complex three-dimensional surface structure to facilitate such tissue integration. A highly porous surface, while it is ideal for tissue ingrowth, presents problems with regard to bacterial contamination. An improved surface is needed which would encourage attachment of cells and tissues to achieve clinical stability without sacrificing the advantages of a smooth surface.

It is thus advantageous to provide a barrier device of dense, hydrophilic PTFE which will provide for selective cell repopulation of bone defects that does not allow the incorporation of cells or fibrous materials, has an improved hydrophilic surface for enhancement of cell attraction and attachment and for improved wetting by body fluids, is easy to remove after extended implantation periods, will not provide a location for contamination by foreign particles or bacteria, will not elicit a foreign-body inflammatory response, does not have the potential to transmit human infectious disease, is soft and supple such that compliance is similar to soft tissues, will facilitate retention of particulate grafting materials, and is convenient to use.

SUMMARY

In accordance with some exemplary embodiments, the present invention provides a medical barrier that includes a sheet of hydrophilic, unsintered substantially unexpanded polytetrafluoroethylene (PTFE) polymer material having a density in a range of about 1.2 gm/cc to about 2.3 gm/cc, and preferably in the range of about 1.45 gm/cc to about 1.55 gm/cc, and having at least one textured surface. In one embodiment, the sheet has one textured surface and one substantially smooth surface, and has substantially uniform strength in all directions.

The sheet of medical barrier of the present invention has a thickness in a range of about 0.125 mm to about 0.25 mm. Preferably, the textured surface is formed by a plurality of indentations formed in the surface of the sheet. The indentations have a depth less than the thickness of the sheet and each indentation has a nominal width of about 0.5 mm. The indentations are distributed substantially uniformly over the surface of the sheet. In some embodiments, the indentations are distributed over the surface of the sheet at about 196 indentations per square centimeter.

The medical barrier of the present invention is particularly well adapted for use in guided tissue regeneration in the repair of bone defects, and particularly in the repair of alveolar bone defects. The barrier prevents the entry of rapidly migrating gingival tissue cells into the defect and allows the alveolar bone to regenerate. During healing, the gingival tissue adheres somewhat to the textured surface of the barrier to anchor the gingival tissue over the barrier, thereby preventing dehiscence or splitting open of the tissue covering the material. However, the high density unexpanded substantially non-porous nature of the medical barrier of the present invention prevents gingival tissue from growing into or through the barrier. Thus, after the bone defect has healed, the barrier may be removed with a minimum of trauma to the gingival tissue.

In contrast to hydrophobic PTFE, it has been found that hydrophilic PTFE membranes exhibit a greater affinity for cellular adhesion, attachment and spreading. In addition, with respect to bone cell interaction with biomaterial surfaces, hydrophilic surfaces have been shown to promote increased mineralization and osteoblastic differentiation as measured by alkaline phosphatase (ALP) activity compared to hydrophobic surfaces. Transmission of body fluids, such as blood and plasma occurs more readily with hydrophilic membranes. Clinically, this results in faster and more predictable soft tissue coverage, improved soft tissue attachment without requiring ingrowth, and fewer wound healing complications when compared to similar devices manufactured from hydrophobic PTFE. Thus, the present invention provides a significant clinical and biological advantage over current, hydrophobic PTFE guided tissue regeneration membranes.

DETAILED DESCRIPTION

Figure 1:
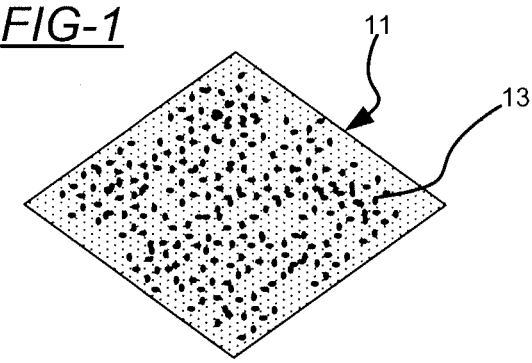
FIG. 1 is a perspective view showing the textured surface of the medical barrier of the present invention.
Figure 2:
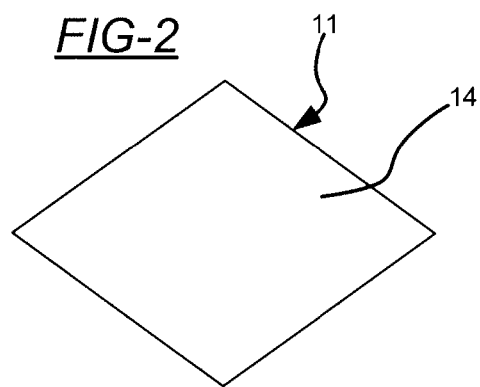
FIG. 2 is a perspective view showing the untextured surface of the medical barrier of the present invention.
Figure 3:
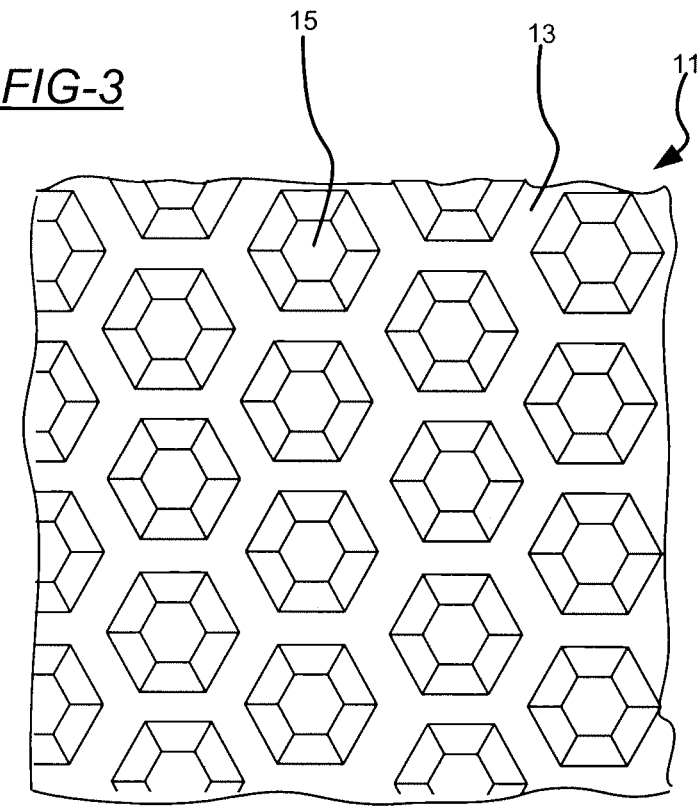
FIG. 3 is an enlarged view of the textured surface of the medical barrier of the present invention.

Referring now to the drawings, and first to FIGS. 1 and 2, a medical barrier according to one embodiment of the present invention is designated generally by the numeral 11. Barrier 11 comprises a sheet of unsintered substantially unexpanded hydrophilic polytetrafluoroethylene (PTFE) polymer. As shown in FIG. 1, barrier 11 includes a textured surface 13, and as shown in FIG. 2, an untextured surface 15. Barrier 11 has a density in the range of about 1.2 gm/cc to about 2.3 gm/cc, and preferably in the range of about 1.45 gm/cc to about 1.55 gm/cc. Barrier 11 has a sheet thickness in the range of about 0.125 mm to about 0.25 mm. As shown in FIG. 3, the textured surface of the exemplary embodiment is formed by a plurality of indentations 15 formed in surface 13 of barrier 11. In some embodiments, indentations 15 may be hexagonal in shape, although other shapes are within the scope of the present invention. The indentations have a depth less than the thickness of the sheet, and in the illustrated embodiment indentations 15 are about 0.15 mm deep. In some implementations, indentations 15 are about 0.5 mm wide.

Indentations 15 are distributed substantially uniformly over surface 13 of barrier 11 at about 150 indentations per square centimeter to about 250 indentations per square centimeter. In accordance with some exemplary implementations, indentations 15 are distributed over surface 13 of sheet 11 at about 196 indentations per square centimeter.

The barrier of the present invention is made by first forming a thin sheet of unsintered PTFE and then embossing the sheet with indentations. PTFE resin is mixed with a lubricant such as mineral spirits to form a paste. The paste is then calendered in multiple passes between rollers to form a thin flat sheet of the desired thickness in the range of about 0.125 mm to 0.25 mm. The calendering is performed multiple times in multiple directions to reduce the thickness of the sheet and to impart substantially uniform strength in all directions to the sheet. The lubricant is removed by drying the sheet at temperature somewhat above the boiling point of the mineral spirit lubricant, but well below the sintering temperature of PTFE, which is about 327 degrees C. The foregoing process steps result in a flat sheet of unsintered PTFE about 0.125 to 0.25 mm thick, having a density in the range of about 1.2 gm/cc to about 2.3 gm/cc, and having substantially uniform strength in all directions. The resulting flat sheet has two substantially smooth surfaces.

After the sheet has been dried, the sheet is embossed to form the indentations in one of its surfaces. In some embodiments, the embossing step may be performed by placing a sheet of patterned polymer mesh on top of the unembossed sheet of unsintered PTFE. The patterned polymer sheet material, such as polyethylene or polypropylene, may be harder and have more compressive strength than the unsintered PTFE material. One such polymer sheet is embodied in a fine pore-size sheet filter material manufactured by Tetko, Switzerland. The polymer sheet has a pattern that is embossed into the polymer sheet. The polymer sheet and the unsintered PTFE sheet are passed together between a pair of rollers, which emboss the pattern of the polymer sheet into one surface of the unsintered PTFE sheet. After embossing, the polymer sheet may be discarded.

After embossing, the sheet may be treated by various methods known in the art to impart hydrophilic characteristics to the membrane surface. These methods include the addition of a second polymer or hydrophilic chemical compound, chemical treatment of the membrane surface, laser etching or glow discharge plasma etching. The surface modified embossed unsintered PTFE sheet may be cut into smaller sheets of various shape and size for packaging and distribution.

The surface modification to make the surface hydrophilic may be applied selectively to the surface. For example, the hydrophilic portion of the surface may be limited only to the central part 14 of the surface. Alternatively, the hydrophilic portion of the surface may be limited to the marginal parts of the surface.

After surface modification, the membrane may be modified further by linking the hydrophilic portion or portions to bioactive molecules, preferably by covalent bonds. Examples of such bioactive molecules include growth factors, cytokines, morphogenetic proteins, cell attractants, adhesion molecules, and the like. The source of such bioactive molecules may be autologous, allogenic, xenogenic or synthetic.

Figure 4:
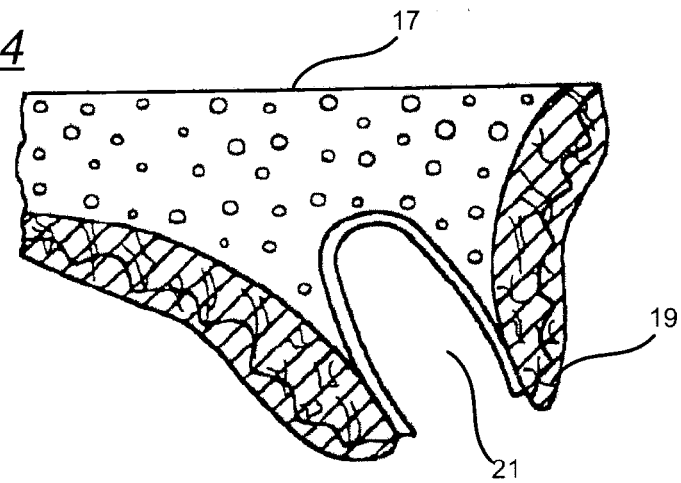
FIG. 4 is a lateral cross-sectional view of a maxillary bony defect resulting from the extraction of a tooth.
Figure 5:
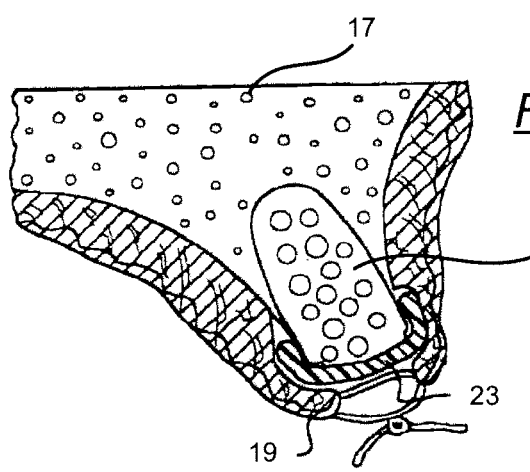
FIG. 5 is a lateral cross-sectional view of the maxillary bony defect of FIG. 4 showing the placement of the medical barrier of the present invention to cover the bony defect with the mucoperiosteal flap sutured over the medical barrier.
Figure 6:
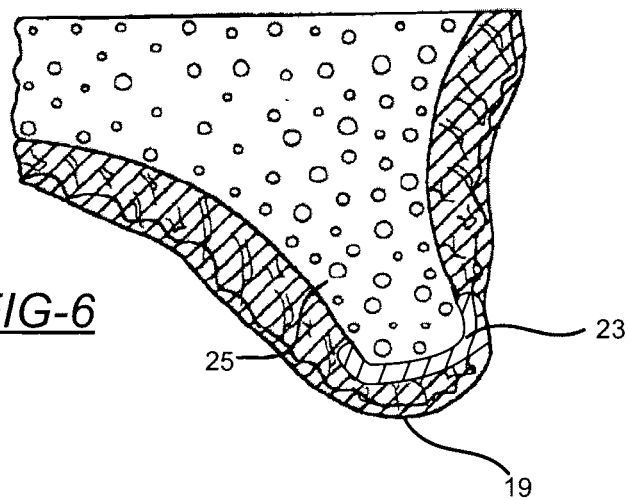
FIG. 6 is a lateral cross-sectional view showing the healed maxillary bony defect of FIG. 4 with the gingival tissue healed over the medical barrier of the present invention.

Referring now to FIGS. 4-6, there is illustrated the manner of use of the barrier of the present invention. FIG. 4 is a lateral cross-sectional view of an adult human maxilla after a tooth extraction. The bone of the alveolar process is designated by the numeral 17. Soft tissue gingiva 19 covers bone 17. A tooth socket is designate by the numeral 21.

Socket 21 is an example of a bone defect. Other examples of bone defects are those caused by periodontal disease, cyst formation, surgery, or trauma. Normal healing of a defect includes migration of foreign cells such as fibroblasts and gingival epithelial cells. As the cells proliferate into the defect, they inhibit bone cell regeneration, which results in overall loss of bone mass. In the case of extractions, the loss of bone mass results in a loss of alveolar ridge profile.

Referring now to FIG. 5, there is shown one method of using the barrier of the present invention. Socket 19 is shown packed with granular particles of hydroxyapatite as a precursor to bone. Those skilled in the art will recognize that other materials or articles, such as endoseouss-type dental implants, may be placed into socket 21. The packed socket 21 is covered with a layer 23 of the barrier of the present invention. The smooth side of the barrier is placed over socket 21 and bone 17. Thus, the textured of the barrier is positioned adjacent the gingival tissue 19. The substantially uniform strength in all directions of the material of the present invention allows the surgeon to shape layer 23 over socket 21 and bone 17. After layer 23 is placed over socket 21 and bone 17, the gingival flaps 19 are sutured over layer 23. Layer 23 holds the hydroxy apatite particles in place in socket 21 during healing and prevents migration of cells and connective tissue into socket 21. However, connective tissue forms a weak attachment with the textured surface of layer 23, without growing through the material. The attachment is weak enough that the layer may be removed after healing without significant trauma but is strong enough to prevent the dehiscence.

Referring to FIG. 6, there is shown the extraction site after healing, but prior to removal of layer 23. As shown in FIG. 6, the alveolar ridge profile 25 is preserved and the gingival tissue 19 is completely healed over ridge 25. Layer 23 may be removed by making a small incision (not shown) in gingival tissue 19 to expose a portion of layer 23. The layer 23 may then be pulled out with forceps or the like. Since the connective tissue attaches only weakly to the hydrophilic textured surface of the material of the present invention, the material may be pulled out easily and without trauma to the patient.

From the foregoing, it may be seen that the medical barrier of the present invention overcomes the shortcomings of the prior art, and is particularly well adapted for use in guided tissue regeneration in the repair of bone defects, as for example in the repair of alveolar bone defects. The barrier prevents the entry of rapidly migrating gingival tissue cells into the defect and allows the alveolar bone to regenerate. During healing, the gingival tissue adheres somewhat to the hydrophilic textured surface of the barrier to anchor the gingival tissue over the barrier, thereby preventing dehiscence or splitting open of the tissue covering the material. However, the high density unexpanded substantially non-porous nature of the medical barrier of the present invention prevents gingival tissue from growing into or through the barrier. Thus, after the bone defect has healed, the barrier may be removed with a minimum of trauma to the gingival tissue.

Aspects of the present invention have been illustrated and described in detail with reference to particular embodiments by way of example only, and not by way of limitation. It will be appreciated that various modifications and alterations may be made to the exemplary embodiments without departing from the scope and contemplation of the present disclosure. It is intended, therefore, that the invention be considered as limited only by the scope of the appended claims.

What is claimed is:

1. A guided tissue regeneration membrane comprising a multi-surfaced polytetrafluoroethylene sheet having a portion of one surface of the polytetrafluoroethylene sheet that is hydrophilic, which renders the membrane surface substantially compatible with water, body fluids, blood and aqueous solutions, wherein the hydrophilic portion is limited to a central portion of the membrane and comprises an embossed portion, wherein embossments of the hydrophilic portion are etched by one or more of glow discharge plasma and a laser.

2. A medical barrier comprising
a multi-surfaced membrane,
wherein the membrane comprises a sheet of high density, unexpanded, unsintered polytetrafluoroethylene,
wherein one surface of the membrane is embossed and treated, after embossing, by addition of one or more of a polymer, a reactive chemical, and an etching of the surface, thereby providing a limited portion of the one surface that is compatible with one or more fluids, and
wherein the medical barrier is adaptable for use in guided tissue regeneration in the repair of bone defects.

3. The medical barrier of claim 2, wherein the limited portion of the one surface is substantially compatible with water.

4. The medical barrier of claim 2, wherein the limited portion of the one surface is substantially compatible with body fluids.

5. The medical barrier of claim 2, wherein the limited portion of the one surface is substantially compatible with blood.

6. The medical barrier of claim 2, wherein the limited portion of the one surface is substantially compatible with water, body fluids, blood and aqueous solutions.

7. The medical barrier of claim 6, wherein the embossed portion is treated with at least one of a hydrophilic polymer and a reactive chemical.

8. The medical barrier of claim 7, wherein the embossed portion is linked via covalent bonds to bioactive molecules.

9. The medical barrier of claim 8, wherein the bioactive molecules include one or more of a growth factor, a cytokine, morphogenetic protein, a cell attractant, and an adhesion molecule.

10. The medical barrier of claim 9, wherein the source of the bioactive molecules is selected from the group consisting of autologous, allogenic, xenogenic and synthetic.

11. A tissue regeneration membrane usable as a medical barrier and comprising a high density polytetrafluoroethylene sheet having a plurality of surfaces, wherein the membrane comprises high density, unexpanded, unsintered PTFE, wherein an embossment of a selected portion of one of the plurality of surfaces is treated by one or more of polymer coating, a chemical reaction, and an etching, thereby making the selected portion of the one surface hydrophilic and substantially compatible with water, body fluids, blood and aqueous solutions, and wherein the medical barrier provides for guided tissue regeneration.

12. The tissue regeneration membrane of claim 11, wherein medical barrier is adapted for use in the repair of bone defects.

13. The tissue regeneration membrane of claim 11, wherein the selected portion of the one surface includes an embossed portion treated with a hydrophilic polymer.

14. The tissue regeneration membrane of claim 11, wherein the selected portion of the one surface is treated by chemical reaction.

15. The tissue regeneration membrane of claim 11, wherein the selected portion of the one surface is treated by etching.

16. The tissue regeneration membrane of claim 15, wherein one of the plurality of surfaces is textured and wherein another of the plurality of surfaces is substantially smooth.

17. The tissue regeneration membrane of claim 11, wherein the selected portion is provided at the periphery of the membrane and comprises a border of the membrane.

18. The tissue regeneration membrane of claim 11, wherein the selected portion is limited to a central portion of the membrane.

19. The medical barrier of claim 2, wherein the embossed portion is treated with a hydrophilic chemical.

20. The medical barrier of claim 2, wherein the embossed portion is laser etched.

21. The medical barrier of claim 2, wherein the embossed portion is etched by glow discharge plasma.

* * * * *